United States Patent
Boyd et al.

(10) Patent No.: US 9,700,043 B2
(45) Date of Patent: Jul. 11, 2017

(54) CORROSIVE INGREDIENT(S)-CONTAINING COMPOSITIONS HAVING REDUCED TOXICITY AND METHOD OF OBTAINING

(71) Applicant: S. C. Johnson & Son, Inc., Racine, WI (US)

(72) Inventors: Kevin N. Boyd, Mt. Pleasant, WI (US); Matthew Michael Petkus, Lake Villa, IL (US); Pablo M. Hernandez, Waukegan, IL (US); Gerald R. Hofmann, Racine, WI (US); Caitlin Y. O'Gara, Arlington Heights, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 14/666,562

(22) Filed: Mar. 24, 2015

(65) Prior Publication Data

US 2015/0264926 A1  Sep. 24, 2015

Related U.S. Application Data (60) Provisional application No. 61/969,597, filed on Mar. 24, 2014.

(51) Int. Cl.
*A01N 37/36* (2006.01)
*A61K 8/39* (2006.01)
(Continued)

(52) U.S. Cl.
CPC ............... *A01N 37/36* (2013.01); *A61K 8/39* (2013.01); *A61K 8/73* (2013.01); *A61K 8/8147* (2013.01);
(Continued)

(58) Field of Classification Search
CPC .... A01N 37/36; A61K 2800/526; A61K 8/39; A61K 8/73; A61K 8/8147; A61Q 19/10
See application file for complete search history.

(56) References Cited

U.S. PATENT DOCUMENTS 6,153,571 A * 11/2000 Komocki ............ C11D 3/2034
510/190
6,767,881 B1 * 7/2004 Griese ...................... C11D 1/72
510/101
(Continued)

FOREIGN PATENT DOCUMENTS

GB        2106927 A      4/1983
WO     WO 97/40125 A1   10/1997

OTHER PUBLICATIONS

Euramid V Cocamide DEA et al. "Euroglyc MD Viscosity Building Properties: Eruglyc MD Shows Optimal Viscosity Building Properties in a Surfactant Solution Based on Sodium Laureth Sulfate and Cocamide DEA Formulation Details." Jan. 1, 2008; URL: http://www.eocgroup.com/sites/default/files/images/ProductFiche%20Euroglyc%20MD.pdf.
(Continued)

*Primary Examiner* — Aradhana Sasan (57) ABSTRACT

Compositions, preferably cleaning compositions, containing at least one component which is corrosive by nature and present at a level to render the compositions corrosive, are provided with reduced corrosivity by increasing the viscosity of the compositions. Reduction in corrosivity of the compositions is provided to a degree so that the compositions are classified as non-corrosive under EPA or OECD/GHS regulations and do not have to be stored in and dispensed from child-resistant packaging and do not require regulated hazard warning labeling.

30 Claims, 4 Drawing Sheets

(51) Int. Cl.
*A61K 8/81* (2006.01)
*A61Q 19/10* (2006.01)
*A61K 8/73* (2006.01)

(52) U.S. Cl.
CPC ........ *A61Q 19/10* (2013.01); *A61K 2800/526* (2013.01)

(56) References Cited

U.S. PATENT DOCUMENTS

| 2002/0173435 | A1 | 11/2002 | Librizzi | |
|---|---|---|---|---|
| 2006/0079415 | A1* | 4/2006 | Kozubal | A61K 8/24 510/119 |
| 2010/0055196 | A1* | 3/2010 | MacGregor | A01N 59/00 424/600 |

OTHER PUBLICATIONS

Regina Cosby et al. "Hand In Glove Handling HPAPIs Safely Change of Power CMOs in High Potency Hand In Glove Handling HPAPIs safely Change of Power CMOs in High Potency Plus: Surfactants—Chemocatalysts—REACH Implementation—Boronic Acids & Esters—Latest News." Jan. 1, 2012 URL: http://www.harke.com/fileadmin/images/chemicals/The_Value_of_Sultaines-_R._Cosby_and_F._Wagner_January_2012.pdf.
Robert L Goldemberg et al. "Use of Anti-Irritants Formulating in Cosmetic Presented Before the Third Congress of the I." Jan. 1, 1965; pp. 317-340, URL: http://journal.scconline.org/pdf/cc1965/cc016n06/p00317-p00340.pdf pp. 321, 335, 337, abstract.
PCT/US2015/022192 International Search Report and Written Opinion dated Jan. 16, 2015.

* cited by examiner

CORROSIVE INGREDIENT(S)-CONTAINING COMPOSITIONS HAVING REDUCED TOXICITY AND METHOD OF OBTAINING

RELATED APPLICATION

This application claims benefit of U.S. Provisional Patent Application Nos. 61/969,597 filed Mar. 24, 2014.

FIELD OF INVENTION

Compositions including ingredient(s) which are corrosive by nature and present at a level to make said compositions corrosive, having a viscosity to render the compositions non-corrosive are described, including a method of providing the non-corrosive compositions. Of particular benefit are cleaning compositions containing antibacterial and/or disinfectant ingredient(s) which are corrosive by nature and whose effect on the composition are rendered non-corrosive by increasing the viscosity of the cleaning compositions.

BACKGROUND OF THE INVENTION

Non-antibacterial and non-disinfectant products in the United States are regulated by the Consumer Product Safety Commission (CPSC), and the CPSC has provisions for risk-based assessments. Antibacterial and disinfectant products, however, are regulated by the United States Environmental Protection Agency (EPA), and the EPA tends to rely on hazard-based classifications (i.e., relies on required testing results and does not take into account potential human exposure and/or how the product is likely to be used). Antibacterial and disinfectant concentrate formulas that could be potentially accessed by a consumer need to be tested to determine toxicity. Therefore, if above certain levels, a product of the formula will require child-resistant packaging and hazard warning labeling since the end-user (i.e., consumer) could be exposed to this concentrated formula. The concentrate, as opposed to the diluted product, therefore must be tested for hazard classifications under EPA regulations. If the concentrate is corrosive, which is likely in order to achieve disinfection upon dilution of the concentrate, child-resistant packaging would be needed, as well as hazard labeling to indicate toxicity. Child-resistant packaging in certain dispensers can be complicated and expensive, e.g., on a trigger spray product.

Therefore, being able to reduce toxicity in compositions containing one or more corrosive ingredients is beneficial in order to change the composition from corrosive to non-corrosive. Products of reduced corrosiveness or toxicity are viewed by consumers as preferable for use for both personal safety and environmental benefits.

SUMMARY OF INVENTION

The invention is directed to products, and a method of providing such products, containing one or more ingredients which are corrosive by nature and present at a level which can render the product corrosive so as to be considered toxic or hazardous for purposes of packaging and labeling, and reducing the corrosiveness or toxicity of such products so that the product is non-corrosive. Special packaging will not then be required and more conventional cautionary labeling appropriate due to the type of product it is can be used for the products. Products for which the invention has been found to be especially beneficial are cleaning products. Cleaning products often include one or more antibacterial and/or disinfectant components. Antibacterial and disinfectant components, such as used in cleaning products, are generally corrosive by nature. The amount(s) of antibacterial and disinfectant component(s) is/are increased in a concentrate thereby increasing the overall corrosivity of the cleaning product. In use, such concentrate products are usually diluted to render the product milder and safer for the end consumer. Thickening a concentrate is often viewed as making the composition stronger, thus, more concentrated and possibly more corrosive.

It has been found, however, that contrary to what might be expected, increasing the viscosity of a cleaning product which includes at least one component which is corrosive in nature and at a level to make the composition corrosive serves to reduce the toxicity, i.e., the corrosivity, of the product and lower absorbance of the product to a degree which renders the product non-corrosive.

The ability to provide a non-corrosive product containing a material previously rendering the product corrosive allows a consumer to be less concerned with use of the product as to safety and allows for packaging which is more convenient to use. In the past, reducing corrosivity of a particular product formula, generally required reducing the amount of or total replacement of any corrosive ingredient(s). The present invention allows the retention of the component which is corrosive by nature as well as the use of the level of the component in the formula needed to provide the desired antibacterial and disinfectant properties in the final product.

In cleaning products, disinfectants and antibacterials are generally corrosive by nature. The invention will be described herein for convenience, but without limiting the nature of the invention, in relation to disinfectants and antibacterials as being the corrosive ingredient. However, the invention is applicable to other ingredients suitable for use in a cleaning composition which are corrosive by nature. The ability to retain such corrosive ingredients as well as maintain the amount level of such ingredients is also beneficial in allowing flexibility in formulating cleaning concentrates and flexibility in the type of delivery system or dispenser that can be used for the composition.

The invention is applicable to cleaning formulas having a pH in a range of about 2 to about 12, thus including substantially both a high pH (e.g., ≥10) and low pH (e.g., ≤4) which are the characteristic basic and acidic pH levels for concentrated cleaning products. Generally, products of the invention will be provided with viscosities from about 100 to about 1,250,000 centipoise (cps), preferably about 1000 to about 12,000 cps. The product formula contains at least one surfactant and/or at least one component which is corrosive in nature (which is usually a disinfectant or antibacterial (which may also be a surfactant in nature) in a cleaning composition). The thickening of the formula to increase its viscosity can be achieved by adding a thickening component which can be one or more thickening agents or blending of two or more ingredients which self-thicken when blended to achieve a desired viscosity. Of the latter type, an example is of the mixing of two types of surfactants together, or by the mixing of a surfactant with a salt (e.g., sodium chloride) to achieve a desired thickness. The degree of thickness or viscosity provided by a particular product formula will be dependent on the level of corrosiveness present in the product and the degree of reduction in corrosivity so as to fall within a non-corrosive classification under EPA regulations or corresponding International test guidelines, e.g., OECD/GHS guidelines (Organization For Economic Co-Operation And Development/Globally Harmonized System Of Classification And Labeling Of Chemicals). For example, a highly corrosive product will generally require a higher viscosity to diminish ocular irritation under EPA testing standards, while a formula barely meeting the level of corrosivity will generally require only a slight increase in viscosity to reduce the corrosiveness present in the product. The critical feature is the ability to change the corrosive nature of the product to a milder, non-corrosive level and not the degree in reduction of corrosivity as a result of reducing the amount of the corrosive agent. The degree of thickness can be affected by the pH of the product formula, but more than the pH of the formula is relevant. The pH can affect the thickening component selected to increase viscosity since certain thickening components work better under certain pH conditions as compared to other pH conditions. So by way of example, to achieve outcomes in the accepted EPA ocular irritation assay to be classified as non-corrosive, i.e., not requiring child-resistant packaging and not requiring hazard labeling due to corrosivity, viscosity can be in a range of about 100 to about 550 cps (looks like a liquid) to about 8000 cps (looks like a jelly) to over about 100,000 cps (a thick gel). Depending on the product and degree of corrosivity of the product, different viscosities will be effective to achieve a non-corrosive assay result. Not all viscosities are suitable for use with all product types and delivery systems. The important element of the invention is to provide a viscosity or thickness that minimizes corrosivity and, thus, ocular irritation under testing, without dramatically impacting the form or composition of the product. The type of dispenser container may also determine the level of viscosity. For example, if a trigger spray dispenser is used, the formula can only be provided with a certain level of viscosity in order to be properly useful in that type of container. If the viscosity is too great, the formula will not dispense well from the trigger sprayer. Other dispensers for formulas of greater viscosity may be, for example, a pump, a squeeze tube, or a water-soluble pouch. Thus, flexibility in formulation is available based on other product characteristics desired.

Cleaning compositions applicable for use in the present invention include drain cleaners, oven cleaners, toilet cleaners, bleach and acid cleaners, automotive care products and other cleaners that include one or more ingredients contained therein considered corrosive by nature and used at a level providing corrosivity. This invention also should be considered useful with insecticide formulas and formulas containing other active component(s) which are corrosive by nature. As described above, the nature of the type of dispensing applicator to be used can also affect the degree of viscosity of the product and vice versa. For example, certain viscosities are preferable for use with a trigger spray dispenser, a squeeze tube, a pump, or a water-soluble pouch.

DESCRIPTION OF PREFERRED EMBODIMENTS

Products including one or more ingredients which are corrosive in nature and present in a product at a level which normally cause ocular irritation are modified to have reduced ocular irritation without replacing the corrosive ingredient(s) and without reducing the amount of the corrosive ingredient(s) used in a product. The level of corrosiveness or the hazards of a product is determined under EPA regulations. EPA toxicity testing is based on determining the level of ocular irritation caused by a product. This EPA standard is used herein to evidence the reduced corrosive nature of products of the invention. The test used is the bovine cornea opacity and permeability (BCOP) method which is an Organization for Economic Co-operation and Development (OECD) validated method for assessing ocular irritation and has recently been accepted by the EPA as an alternative to the traditional Draize animal test. The BCOP test method is described in the "OECD Guidelines For The Testing Of Chemicals", No. 437, adopted Jul. 26, 2013 and entitled "Bovine Corneal Opacity and Permeability Test Method for Identifying i) Chemicals Inducing Serious Eye Damage and ii) Chemicals Not Requiring Classification for Eye Irritation or Serious Eye Damage". The BCOP method is also described in the EPA policy document entitled "Use of an Alternate Testing Framework for Classification of Eye-Irritation Potential of EPA Pesticides Products", Office of Pesticide Programs, US EPA, May 13, 2014 available at www.epa.gov/pesticides/science/eye-irritation.html). The materials and method of the BCOP method as used with the examples below is as follows:

BCOP Materials and Method

Step 1—Corneal Excision. Upon receipt, eyes are examined and corneas that are free of defects are excised.

Step 2—Mounting. Corneas are mounted into chambers and incubated for one (1) hour at 32±1° C. in complete minimum essential medium (cMEM).

Step 3—Initial Opacity. The cMEM is removed and refilled and the initial opacity is read on an opacitometer.

Step 4—Test Article Exposure. 750 µL of test substance is applied to the anterior chamber for 10 minutes at 32±1° C.

Step 5—Rinsing. Corneas are rinsed thoroughly to remove the test substance and incubated for two (2) hours before a final opacity reading.

Step 6—Fluorescein Addition. One (1) ml of a 4 mg/ml fluorescein solution is added to the epithelial side of the corneas and incubated at 32±1° C. for 90 minutes.

Tests have shown a reduction in corrosive classification in products of the invention where increasing viscosities correlate to decreasing ocular irritation. For example, surfactants deemed corrosive by its supplier can be reduced to baseline levels of irritation when the mixture to provide the product containing the surfactant is thickened to a gel-like product. In other products, however, even slight modification of the viscosity of a product mixture is seen to reduce a product from corrosive to non-corrosive. Thus, liquid spray products can also be modified.

The viscosity of a composition having a pH of about 2 to about 12 containing at least one surfactant and/or at least one component which is corrosive by nature (e.g., disinfectant, antibacterial, insecticide, etc.), which also can be a surfactant, is a particularly important feature for providing a product having a reduced corrosivity, in particular reduced to a level so that the product does not require child-resistant packaging or regulated hazard labeling. The invention is useful both with diluted ready-to-use compositions or concentrate composition where the pH is generally less than or about 4 or about 10 or greater. The formula of the product can have a thickening component added thereto to increase viscosity where the thickening component is either one or more thickening agents or can be self-thickening blend based on a blend of two or more components, for example, mixing two types of surfactants together or by mixing a surfactant with a salt, for example sodium chloride (NaCl), to achieve a desired thickness or viscosity.

Preferred compositions suitable for use with the invention are cleaning compositions, especially concentrated cleaning compositions. Based on the concentrated nature of the composition, when the composition includes a component which is corrosive by nature, usually a disinfectant or antibacterial component, the corrosivity of the product is high resulting in it being classified under EPA regulations as a product requiring child-resistant packaging (which can be expensive and complicated to use) and/or special hazard labeling. Both of these are undesirable as to cost and consumer perception of product safety.

In cleaning compositions of the above type, the pH thereof is generally clearly acidic, i.e., a pH of about or less than 4, or highly basic, i.e., a pH of about or greater than 10. Concentrated acidic and alkaline cleaners generally include about or greater than 12 wt. % (based on actives) acid component and about or greater than 1 wt. % (based on actives) alkalinity and are readily diluted in water for final use.

Viscosities of cleaning compositions can range from about 100 to about 1,250,000 centipoise (cps), preferably about 1000 to about 12,000 cps, and more preferably about 1000 to about 8000 cps. Viscosity as described herein is based on test measurements using a Brookfield Viscometer in accordance with Brookfield requirements as to conditions for use, e.g., the spindles, rpms (revolutions per minute) and temperature used. The measurements herein (unless stated otherwise) using the Brookfield Viscometer are with a #1 spindle at 12 rpm at 77° F. (25° C.). Viscosity of a particular cleaning product is based on various factors, including and primarily on the degree of corrosivity of the formula and the pH of the formula.

For example, for acidic formulas of a formula having (1) a pH of about 6 or lower preferably has a viscosity of about 100 to about 50,000 cps, (2) of a pH of about 5 or lower preferably has a viscosity of about 125 to about 100,000 cps, (3) a pH of about 4 or lower preferably has a viscosity of about 1000 to about 12,000 cps. Basic formulas, for example, of a formula having (1) a pH of about 8 or higher preferably have a viscosity of about 100 to about 175,000 cps, (2) a pH of about 9 or higher have a viscosity of about 125 to about 450,000 cps, and (3) a pH of about 10 or higher preferably have a viscosity of about 1000 to about 12,000 cps.

Surfactants suitable for use can include nonionic, anionic, cationic and amphoteric/zwitterionic surfactants. Cationic surfactants are known to have disinfecting properties.

Examples of nonionic surfactants suitable for use in the formula include, but are not limited to, ethoxylated alcohols (including branched, linear, and semi-branched), alkyl phenol ethoxylates, alkyl phenol propoxylates, sorbitol propoxylates, alcohol ethylene oxide- and propylene oxide-containing surfactants, alkyl polyglucosides (APGs), fatty alcohol polyglycol ethers, and glycerol ethoxylates.

The nonionic ethoxylated alcohol surfactants preferred for use have a carbon chain length of C6-C24, more preferably of C12-C18, and ethylene oxide (EO) units of 5-24. The nonionic ethoxylates can be linear or branched, although linear are preferred. Examples of nonionic ethoxylated surfactants suitable for use in the concentrated cleaning composition include alkyl polyethylene glycol ethers, such as sold by Sasol Corp. or Huntsman, e.g., SURFONIC L 12-8. Other examples of nonionic surfactants suitable for inclusion are NEODOL 91-6 and NEODOL 91-8 as sold by Shell Chemicals, GENAPOL UD 070 or 080 as sold by Clariant Corp., and TERGITOL 15-S-9 as sold by DOW Chemical. Propylene oxide surfactants base nonionics can also be used. Such only are useful as a low foaming surfactant. Preferred nonionic surfactants are straight or branched C8 to C18 ethoxylated alcohols having 2 to 12 ethylene oxide units. The carbon chain length in the ethoxylated alcohols can be the same or a mixture.

Examples of anionic surfactants suitable for use in the formula include, but are not limited to, linear carbon chain sulfates, alcohol ether sulfates, alkyl benzene sulfonates, alcohol sulfates, alkyl- and alkylaryl-alkoxylated carboxylic acid, and the acid forms of these anionic surfactants, for example, linear alkyl benzene sulfonic acid (LABSA), etc. Preferred examples of linear alkyl benzene sulfonic acids suitable for use include sodium dodecyl benzene sulfonic acid as well as the acid version, and the linear alkyl benzene sulfonic acids sold under the trade name BIOSOFT as sold by Stepan Co.

Examples of cationic surfactants suitable for use in the formula include, but are not limited to, quaternary amines including but not limited to, n-alkyl dimethyl benzyl ammonium chloride, n-alkyl dimethyl ammonium chloride, n-alkyl dimethyl benzyl ammonium chloride (and) dialkyl dimethyl ammonium chloride, and dialkyl dimethyl ammonium chloride. A preferred quaternary compound is sold by Stepan under the trade name BTC 2125.

Examples of amphoteric/zwitterionic surfactants suitable for use in the formula include, but are not limited to, betaines, sultaines and glycines. Suitable betaines for use are sold by Croda. Further amphoteric surfactants having antimicrobial properties are suitable for use, such as described in U.S. Pat. No. 4,769,169, which is incorporated herein by reference.

Surfactant(s) are present in a range of about 3 to about 70 wt. %, preferably about 3 to about 60 wt. %. In a concentrate composition, the amount of surfactant is preferably present in an amount of at least about 10 wt. % at the lower end of the range.

Examples of disinfecting components that can be used in a formula in the acid range are organic and mineral acids including, but are not limited to, lactic acid, citric acid, glycolic acid, malic acid, sodium acid sulfate, hydrochloric acid, formic acid, oxalic acid, sulfamic acid, sulfuric acid, methane sulfonic acid, sodium acid sulfate, hydrogen peroxide, linear alkyl benzene sulfonic acid, acetic acid, phosphoric acid, sulfuric acid, or solvents such as, for example, isopropanol propylene glycol, and quaternary amines, such as n-alkyl dimethyl benzyl ammonium chloride, n-alkyl dimethyl ethylbenzyl ammonium chloride, n-alkyl dimethyl benzyl ammonium chloride (and) dialkyl dimethyl ammonium chloride, and dialkyl dimethyl ammonium chloride.

Examples of disinfecting components that can be used in a formula in the basic range include, but are not limited to, organic amines, especially quaternary amines such as, for example, n-alkyl dimethyl benzyl ammonium chloride, n-alkyl dimethyl ethylbenzyl ammonium chloride, n-alkyl dimethyl benzyl ammonium chloride (and) dialkyl dimethyl ammonium chloride, and dialkyl dimethyl ammonium chloride; bleach such as, for example, sodium hypochlorite; or solvents such as, for example, isopropanol propylene glycol; and hydroxides such as, for example, sodium hydroxide and potassium hydroxide.

Disinfecting components are generally present in an amount of 0.05 to about 5 wt. %, preferably about 0.1 to about 2.5 wt. %. In a concentrate composition, the disinfecting component is present in an amount of at least 1 wt. % at the lower end of the range and up to about 50 wt. %.

Solvent(s) are optional, but preferred in cleaning compositions since they enhance cleaning. Solvents suitable for use can be water-soluble or water-miscible. The non-aqueous solvent is preferably shorter chain (e.g., C4 to C8) alkylene glycols or alkylene glycol ethers, although other solvents are also useful. Examples of alkylene glycols, alkylene glycol ethers, and other solvents suitable for inclusion in the concentrated cleaning composition include hexylene glycol, hexylene glycol ether, benzyl alcohol, phenyl glycol ether, propyl butyl ether and hexyl glycol ether. A water-soluble solvent can be present in place of or together with water. Examples of water-soluble solvents that can be used in place of or together with water are butyl glycol, hexylene glycol, polypropylene glycol, as well as water-soluble glycol ethers such as propylene butyl ether, and C3-C5 alcohols, e.g., isopropanol and propyl alcohol.

Solvent(s) are generally present in an amount of from 0.5 to about 10 wt. %, preferably from about 2 to about 10 wt. %. When in a concentrate composition, the solvent(s) are present in an amount of at least about 2 wt. % at the lower end of the range.

Examples of thickening components suitable for use in a formula include, but are not limited to, anionic thickeners, for example, rheology modifying polymers including acrylate water soluble thickeners, such as preferably CARBOPOL EZ-2, a cross-linked acrylic acid homopolymer, from Lubrizol Corp., acrylate thickeners such as RHEOVIS from BASF Corp., shear thinning polymers, e.g., the ACUSOL products sold by Dow Chemicals, or other cross-linked polyacrylate polymers; sodium xanthan gum, sodium alginate, and sodium carboxymethylcellulose; nonionic thickeners such as POLYOX (polyethylene glycol of various molecular weights) with the preferred being WSR-3000 from the Dow Corp., cellulose thickeners such as hydroxyethyl cellulose sold under the trade name NATROSOL 250HHR from Aqualon Corp., and other cellulose thickeners such as METHOCEL and WALOCELL as sold by Dow Chemical; and other examples of thickeners suitable for use include VANGEL, a magnesium aluminum silicate, from Vanderbilt, certain clays, e.g., bentonite, disteardimonium hectorite clay, smectite clays from Mirasol Corp., etc.; and various associative thickeners from Dow Chemical and BASF Corp.; natural gums, such as guar gum, alginate gum, xanthan gums (various modified) and carrageenan gum; acrylic polymers; polyethylene glycol; ethoxlated amides, e.g., CRYSTASENSE HP-5 as sold by Croda Corp.; and betaines, e.g., MONA AT-1200 as sold by Croda Corp. Any of these thickeners can also be combined to meet specific rheology (shear thinning, shear thickening, pseudo plastic) and stability needs.

Thickening of a formula can also be achieved by, but is not limited to, mixing a salt (for example, sodium chloride) to a surfactant, such as sodium laureth sulfate (SLES).

Another way to thicken a formula is by, but not limited to, providing a blend of two or more ingredients together, such as two surfactants. An example of this method is blending ethoxylated undecyl alcohol with fatty alcohol polyglycol ether based on C16/C18 alcohol (e.g., GENAPOL T250 as sold by Clariant). A preferred thickening agent for acids is the use of a surfactant blend using C11 oxo-alcohol polyglycol ether with 7EO (GENAPOL UD 070 as sold by Clariant) and C16/C18 fatty alcohol polyglycol with 25 moles of EO (GENAPOL T-250 P as sold by Clariant). These surfactants are used in ratios of 5:1 to 1:5. For a basic system, the use of an acrylate polymer having an average molecular weight of 500,000 (e.g., CARBOPOL EZ-2 as sold by Lubrizol) are used in an amount in a range of about 0.5 to about 5.0 wt. %.

The fragrance component can be one or a combination of fragrances, natural or synthetic. The fragrance component is generally present in an amount of from about 0.1 wt. % to about 10 wt. % In a concentrate composition, the fragrance component is preferably present in an amount of at least about 5 wt. % at the lower end of the range.

Water as present in the composition can be deionized water, reverse osmosis water, tap water or the like. Water, when present, is generally present in an amount greater than zero to about 95 wt. %, preferably greater than zero to about 70 wt. % and more preferably from about 10 to about 70 wt. %

While pH adjustment may be necessary, a pH adjuster per se is not required to provide pH adjustment because pH adjustment can occur through other components, such as the corrosive component or the surfactant. Examples of such components include monoisopropanolamine (MIPA) and sodium lauryl alkane benzene sulfonic acid.

Set forth below are specific examples of formulas of the invention, as well as a comparative example. EPA regulations currently require testing for just about everything that is registered with the EPA. Generally, with aggressive chemistries (i.e., sodium hypochlorite) or formulations that are believed to be corrosive, in the absence of testing, the product would be classified as corrosive. The GHS guidelines specifically provides that 3 wt. % of a corrosive ingredient means that the formulation is considered corrosive unless proven otherwise with testing. In the United States, OSHA has adopted GHS guidelines under HazCom 2012. OSHA regulates the classification of a product as to the safety data sheet using GHS standards and the EPA, for a registered product, regulates the product and product label. Accordingly, the formulations below including 15 wt. % and 20 wt. % of a corrosive material (i.e., lactic acid) would be considered corrosive under GHS and OSHA guidelines in the absence of testing.

EXAMPLES

Example 1

Non-Corrosive Under BCOP Test

| Ingredient | Function | Wt. % |
| --- | --- | --- |
| Lactic Acid FCC (88% active) | Disinfectant | 20 (17.6) |
| Fatty Alcohol Polyglycol Ether Based on C16/C18 Alcohol | Cleaning/Thickening | 20 |
| Linear Alkyl Benzene Sulfonic Acid | Cleaning | 17.5 |
| Ethoxylated Undecyl alcohol | Cleaning | 32.15 |

-continued

| Ingredient | Function | Wt. % |
| --- | --- | --- |
| Dipropylene Glycol N-Propyl Ether | Cleaning/Solvent | 2.25 |
| Propylene Glycol N-Butyl Ether | Cleaning/Solvent | 2.25 |
| Deionized Water | Solvent | 4.5 |
| Fragrance | Fragrance | 1.35 |

Example 1 has a pH=2.4 and a viscosity=550 cps.

Example 2

Non-Corrosive Under BCOP Test

| Ingredient | Function | Wt. % |
| --- | --- | --- |
| Lactic Acid (88% active) | Disinfectant | 15.7 (13.82) |
| Alkyl Polyglycoside 425 N | Cleaning | 6.9 |
| Linear Alkyl Benzene Sulfonic Acid | Cleaning | 2.2 |
| Ethoxylated Alcohol | Cleaning | 8.0 |
| Dipropylene Glycol N-Propyl Ether | Solvent/Cleaning | 1.76 |
| Propylene Glycol N-Butyl Ether | Solvent/Cleaning | 1.76 |
| Monoisopropanolamine (MIPA) (99% active) | pH Adjuster | 3.8 (3.76) |
| Deionized Water | Solvent | 57.51 |
| Fragrance | Fragrance | 1.2 |
| Xanthan Gum | Thickener | 1.17 |

Example 2 has a pH=3.35 and a viscosity=143 cps.

Example 3

Corrosive Under BCOP Test

| Ingredient | Function | Wt. % |
| --- | --- | --- |
| Lactic Acid (88% active) | Disinfectant | 15.7 (13.82) |
| Alkyl Polyglycoside 425 N | Cleaning | 6.9 |
| Linear Alkyl Benzene Sulphonic Acid | Cleaning | 2.2 |
| Ethoxylated Alcohol | Cleaning | 8.0 |
| Dipropylene Glycol N-Propyl Ether | Solvent/Cleaning | 1.76 |
| Propylene Glycol N-Butyl Ether | Solvent/Cleaning | 1.76 |
| Monoisopropanolamine (MIPA) (99% active) | pH Adjuster | 3.8 (3.76) |
| Deionized Water | Solvent | 58.68 |
| Fragrance | Fragrance | 1.2 |

Example 3 has a pH=3.34 and a viscosity=similar to water.

Example 4

| Ingredient | Function | Wt. % |
| --- | --- | --- |
| Water | Water | 97 |
| CARBOPOL ® EZ-2 (a cross-linked acrylic acid homopolymer) | Thickener | 1 |
| Sodium Hydroxide (50% Solution) | Base | 2 (1) |

Example 4 has a pH=12.3 and a viscosity (measured by Brookfield LVT, spindle 4, speed 30 rpm)=8000 cps.

Figure 1:
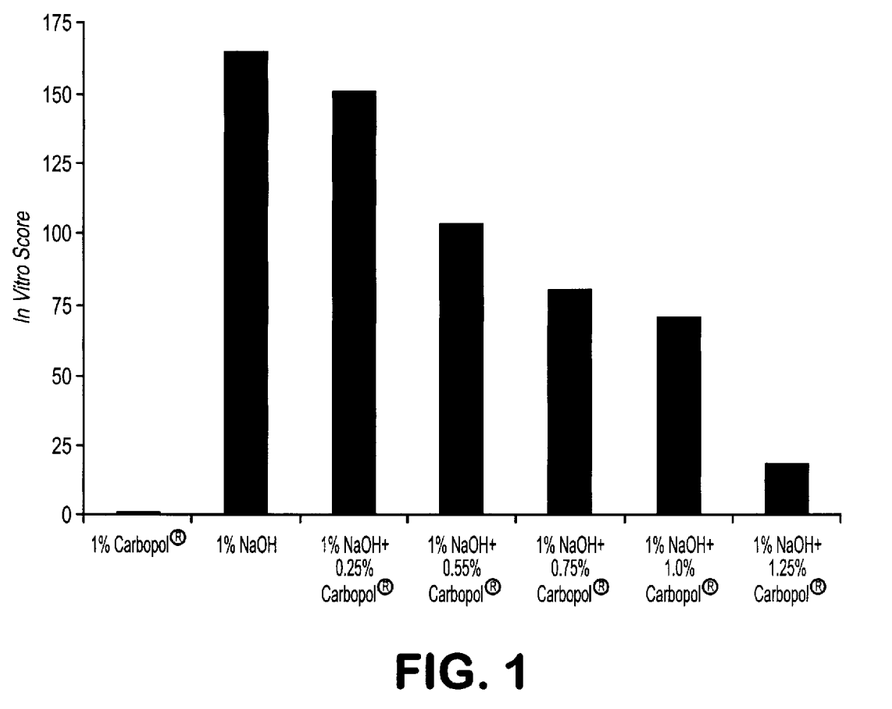
FIG. 1 graphically illustrates test results as to alkaline cleaning formulas showing that ocular irritation diminishes as viscosity increases.

Formulas of the same ingredients as in Example 4 were also tested with lower or higher amounts of CARBOPOL® EZ-2 with respective adjustments in the water concentration. The BCOP assay (n=3 corneas per sample) was performed for 1% sodium hydroxide solutions thickened with an increasing amount of CARBOPOL® EZ-2 to modify the viscosity of the solution. The viscosities of the 0.25% solution was ~4 cps, of the 0.55% solution ~10 cps, of the 0.75% solution ~200 cps, of the 1.0% solution (shown above) ~8,000 cps, (each of the former being measured by Brookfield LVT, spindle 1, speed 30 rpm) and of the 1.25% solution ~18,700 cps (being measured by Brookfield LVT, spindle 4, speed 30 rpm). In addition, CARBOPOL® EZ-2 was tested by itself to assess whether the thickener was contributing to eye irritation (it was not) and 1% NaOH in water was assessed separately and was found to be corrosive. The results of this testing showing that ocular irritation diminishes as the viscosity increases are illustrated in the graph shown in FIG. 1. The EPA and OECD classification criteria for ocular irritation using the BCOP assay for the results described above and shown in FIG. 1 are as follows:

| EPA Use of BCOP | OECD/GHS Use of BCOP |
| --- | --- |
| In vitro score ≥ 75 = Category I | In vitro score > 55 = Category I |
| In vitro score < 75 = Category II | In vitro score ≤ 3 = Not Classified |
| Not used for Category III or IV prediction | In vitro score > 3 but ≤ 55 = no prediction, perform another test |

The four eye irritation categories of the EPA are Toxicity Categories I—Danger, II—Warning, III—Caution, and IV—Caution. Categories I, II, and III have prescribed label precautionary language. Category IV does not require labeling statements. Below is mean data regarding the BCOP assay as shown in FIG. 1 and Example 2.

Mean Data Re BCOP Assay as Shown in FIG. 1 and Example 2

| Designation | Conc. | Exposure Time | Opacity Value | $OD_{490}$ Value | In Vitro Score | pH |
| --- | --- | --- | --- | --- | --- | --- |
| Carbopol | Neat | 10 minutes | 1.3 | 0.000 | 1.3 | 3.5 |
| Xanthan Gum | Neat | 10 minutes | 0.3 | −0.002 | 0.3 | 5.0 |
| Carbopol 0.75% | Neat | 10 minutes | 31.7 | 0.682 | 41.9 | 14.0 |
| Carbopol 1.25% | Neat | 10 minutes | 5.0 | 0.888 | 18.3 | 12.5 |
| Carbopol 0.25% | Neat | 10 minutes | 115.0 | 2.390 | 150.9 | 14.0 |
| Carbopol 0.55% | Neat | 10 minutes | 67.0 | 2.459 | 103.9 | 14.0 |
| Ethanol (Control) | NA | 10 minutes | 28.7 | 0.899 | 42.2 | NA |

Figure 2:
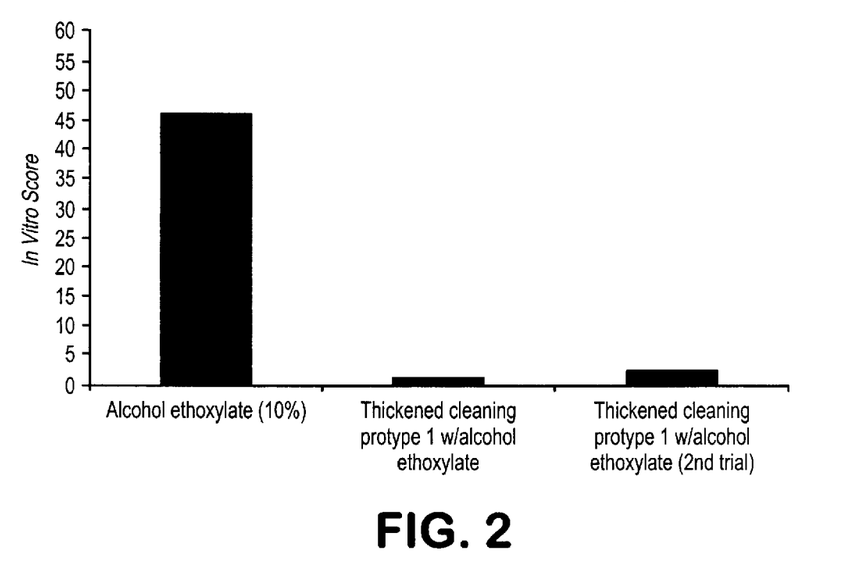
FIG. 2 graphically illustrates test results showing that the viscosity of certain cleaning products tested can attenuate ocular irritation.

FIG. 2 further shows that the viscosity of cleaning products can attenuate irritation. The OECD protocol TG437 specifies that surfactant materials should be tested at 10% w/v dilution in the OECD assay. An alcohol ethoxylate surfactant that is classified as corrosive to the eye by the supplier did not meet the threshold of corrosivity. Under the GHS of the OECD, if a Category I eye irritant is found in a formula at a concentration of ≥3%, then the formula is considered corrosive unless tested. In a thickened cleaning product as described above containing a surfactant with >3% of an alcohol ethoxylate, if testing were not performed, the composition would be considered corrosive. However, following testing using the BCOP method, the BCOP results met the OECD/GHS criteria for "no classification", i.e., an in vitro score of 0-3. Although 0-3 is a very small range, this result was reproducible in a second testing several months after the first testing (in vitro scores were 1.0 and 2.0 in the first and second testings respectively.

Figure 3:
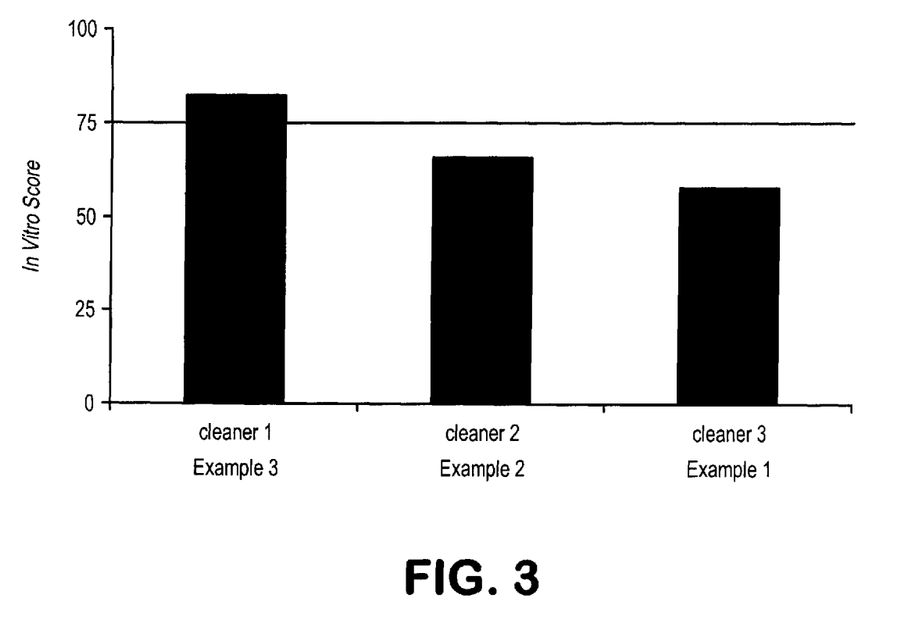
FIG. 3 graphically illustrates results of BCOP assays as to Examples 1-3.
Figure 4:
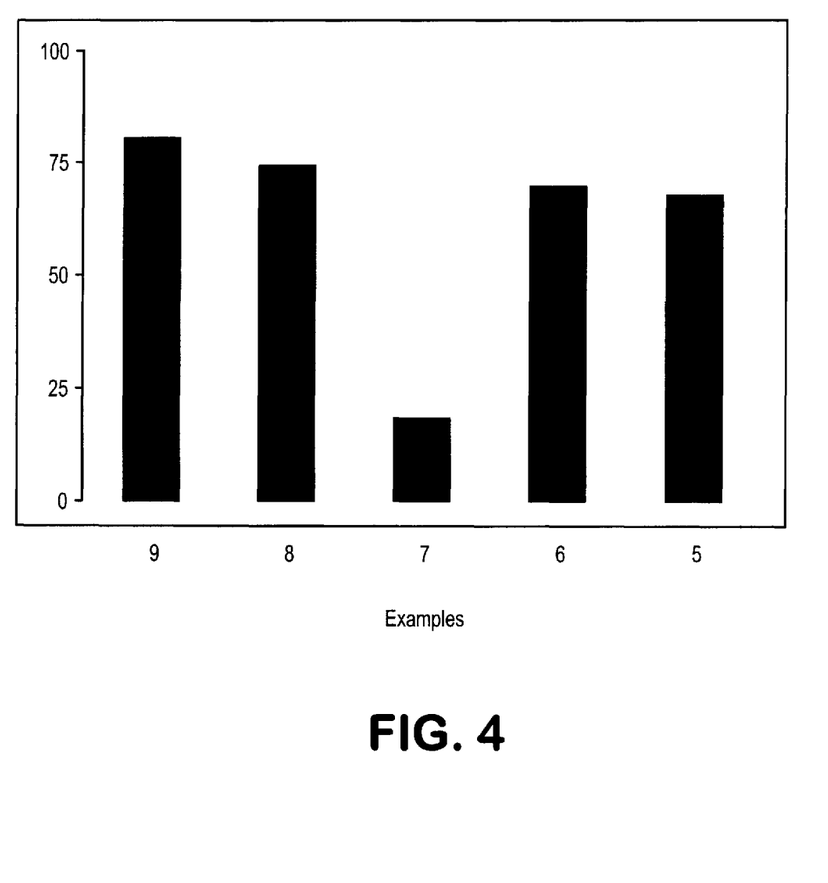
FIG. 4 graphically illustrates results of BCOP assays as to Examples 5-9.
Figure 5:
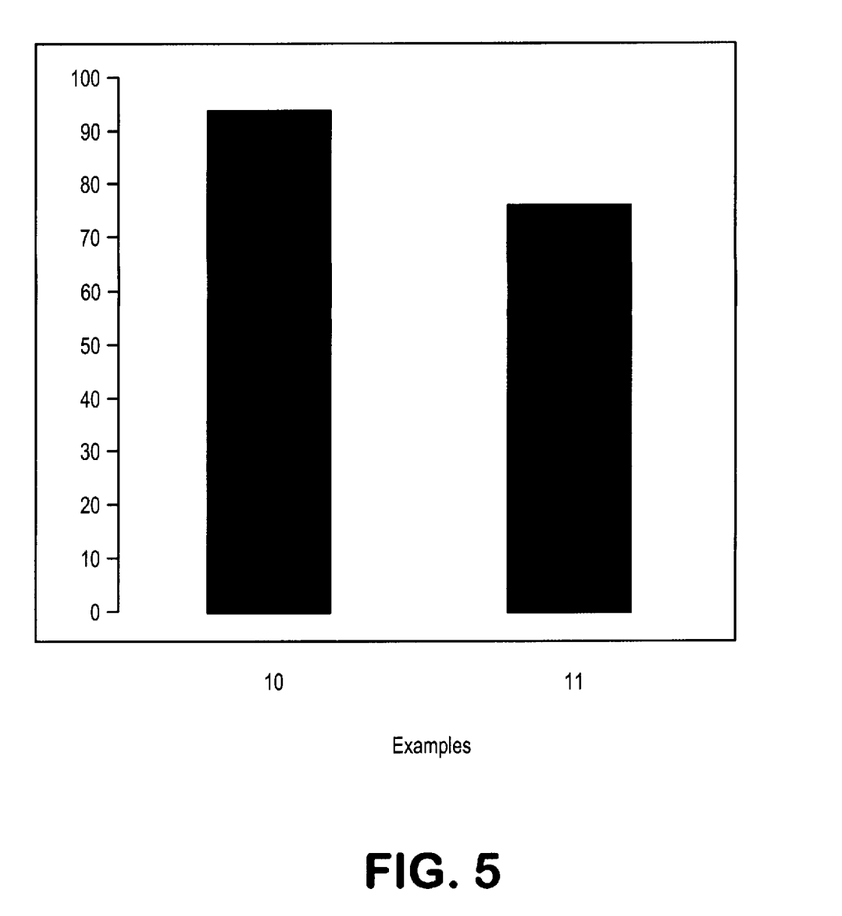
FIG. 5 graphically illustrates results of BCOP assays as to Examples 10-11.

As shown in FIG. 3, Example 3 above is denoted as cleaner 1, Example 2 above is denoted as cleaner 2, and Example 1 above is denoted as cleaner 3. The line on the graph is shown the threshold that the EPA has defined for corrosivity, i.e., an in vitro score of ≥75 is considered EPA Category I (i.e., irreversible eye damage) and requires child-resistant packaging.

Other examples of compositions of the invention are set forth below.

| Ingredients | Example 5 Wt. % | Example 6 Wt. % | Example 7 Wt. % | Example 8 Wt. % | Example 9 Wt. % |
|---|---|---|---|---|---|
| Deionized Water | 68.14 | 68.66 | 68.98 | 69.23 | 69.38 |
| Xanthan Gum | 1.25 | 0.75 | 0.3 | 0.15 | — |
| Na LABSA[1] | 2.2 | 2.2 | 2.2 | 2.2 | 2.2 |
| SURFONIC L12-8[2] | 8 | 8 | 8 | 8 | 8 |
| Propylene Butyl Ether | 1.76 | 1.76 | 1.76 | 1.76 | 1.76 |
| DiPropylene Propyl Ether | 1.76 | 1.76 | 1.76 | 1.76 | 1.76 |
| Fragrance | 1.2 | 1.2 | 1.2 | 1.2 | 1.2 |
| Lactic Acid | 15.7 | 15.7 | 15.7 | 15.7 | 15.7 |
| Viscosity @ 77° F. With #2 Spindle @ 12 rpms | 8250 | 3750 | 1770 | 150 | <10 |
| pH | 2.12 | 2.07 | 2.76 | 2.02 | 1.96 |
| BCOP Score | 66.7 | 69.3 | 18.4 | 73.7 | 80.1 |

[1]Na LABSA = Sodium Linear Alkyl Benzene Sulfonic Acid
[2]SURFONIC L12-8 = A water-soluble nonionic ethoxylated alcohol which is an 8-mole ethoxylate of linear primary 10-12 carbon number alcohol

| Ingredients | Example 10 Wt. % | Example 11 Wt. % |
|---|---|---|
| Deionized Water | 36.65 | 35.35 |
| CARBOPOL EZ-2[1] | — | 1.3 |
| Na LABSA[2] | 17.5 | 17.5 |
| SURFONIC L12-8[3] | 20 | 20 |
| Propylene Butyl Ether | 2.25 | 2.25 |
| Propylene Propyl Ether | 2.25 | 2.25 |
| Fragrance | 1.35 | 1.35 |
| Lactic Acid | 20 | 20 |
| Viscosity @ 77° F. With #2 Spindle @ 12 rpms | <25 | 1350 |
| pH | 2.28 | 2.26 |
| BCOP Score | 93.4 | 74.8 |

[1]CARBOPOL EZ-2 Polymer = Rheology modifying polymer which is a cross-linked acrylic acid homopolymer
[2]Na LABSA = Sodium Linear Alkyl Benzene Sulfonic Acid
[3]SURFONIC L12-8 = A water-soluble nonionic ethoxylated alcohol which is an 8-mole ethoxylate of linear primary 10-12 carbon number alcohol

| Ingredients | Example 12 Wt. % |
|---|---|
| Deionized Water | 33.65 |
| POLYOX WSR-3000 (PEG)[1] | 3 |
| Na LABSA[2] | 17.5 |
| SURFONIC L12-8[3] | 20 |
| Propylene Butyl Ether | 2.25 |
| Dipropylene Propyl Ether | 2.25 |
| Fragrance | 1.35 |
| Lactic Acid | 20 |
| Viscosity @ 77° F. With #2 Spindle @ 12 rpms | 1280 |
| pH | 2.35 |
| BCOP Score | 76 |

[1]POLYOX WSR 3000 = water-soluble polyethylene oxide polymer
[2]Na LABSA = Sodium Linear Alkyl Benzene Sulfonic Acid
[3]SURFONIC L12-8 = A water-soluble nonionic ethoxylated alcohol which is an 8-mole ethoxylate of linear primary 10-12 carbon number alcohol The following are further examples of formulations using other thickening components.

| Ingredients | Example 13 Wt. % | Example 14 Wt. % | Example 15 Wt. % |
|---|---|---|---|
| Deionized Water | 59.75 | 57.25 | 81.15 |
| NATROSOL 250HHR P[1] | 0.5 | 3 | 1.5 |
| Na LABSA[2] | 2.2 | 2.2 | — |
| SURFONIC L12-8[3] | 8 | 8 | 8 |
| BTC 2125[4] | 8 | 8 | 8 |
| Propylene Butyl Ether | — | 2.25 | — |
| Propylene Propyl Ether | — | 2.25 | — |
| Fragrance | 1.35 | 1.35 | 1.35 |
| Lactic Acid | 15.7 | 15.7 | — |
| Viscosity @ 77° F. With #2 Spindle @ 12 rpms | 25 | 2140 | 225 |
| pH | 2.35 | 1.61 | 4.3 |

[1]NATROSOL 250HHR = Hydroxyethylcellulose polymer
[2]Na LABSA = Sodium Linear Alkyl Benzene Sulfonic Acid
[3]SURFONIC L12-8 = A water-soluble nonionic ethoxylated alcohol which is an 8-mole ethoxylate of linear primary 10-12 carbon number alcohol
[4]BTC 2125 = C12/C14 Alkyl Dimethyl Ethylbenzyl Ammonium Chloride and C12-C18 Alkyl Dimethyl Benzyl Ammonium Chloride

| Ingredients | Example 16 Wt. % | Example 17 Wt. % |
|---|---|---|
| Deionized Water | 70.95 | 69.95 |
| CRYSTASENSE HP-5[1] | 4 | 5 |
| SURFONIC L12-8[2] | 8 | 8 |
| Fragrance | 1.35 | 1.35 |
| Lactic Acid | 15.7 | 15.7 |
| Viscosity @ 77° F. With #2 Spindle @ 12 rpms | 392 | 3750 |
| pH | 2.17 | 1.97 |

[1]CRYSTASENSE HP5 = Rheology Modifying polyalkyleneoxy terminated polyamide having a typical molecular weight of 19,000, and is described in U.S. Pat. No. 6,399,713 and EP Patent No. 1358248B
[2]SURFONIC L12-8 = A water-soluble nonionic ethoxylated alcohol which is an 8-mole ethoxylate of linear primary 10-12 carbon number alcohol The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:
1. A composition having reduced corrosivity including one or more ingredients corrosive by nature, comprising—
   (a) at least one surfactant;
   (b) at least one component which is corrosive by nature and present in an amount which renders said composition corrosive in absence of (c), wherein if one or more of said at least one surfactant is corrosive by nature at a level to make the composition corrosive, said at least one component which is corrosive by nature is optional;
(c) a thickening component comprising (1) at least one thickening agent or (2) a blend of two or more components which self-thicken when present as a blend, wherein said thickening component is present to provide a viscosity to said composition so that said composition is non-corrosive;
(d) one or more of water and at least one solvent; and
(e) optionally, a fragrance component;
wherein said composition has a pH of about 2 to about 12;
wherein said composition has a viscosity in a range of about 100 to about 1,250,000 centipoise (cps);
wherein said composition which is initially corrosive is modified to have a level of ocular irritation reduced as compared to said composition not containing said thickening component; and
wherein in absence of said thickening component, said level of ocular irritation of said composition falls into a category under a bovine cornea opacity and permeability (BCOP) method which characterizes said composition as corrosive.

2. The composition of claim 1 wherein said fragrance component is present in an amount of about 0.1 to about 10 wt. %.

3. The composition of claim 1 wherein said at least one solvent is present in an amount of about 0.5 to about 10 wt. %.

4. The composition of claim 1 wherein said viscosity is in a range of about 1000 to about 12,000 cps.

5. The composition of claim 1 wherein said composition is a cleaning composition.

6. The composition of claim 5 wherein said cleaning composition is present in concentrate form and is diluted in use, wherein said pH of said concentrate form is (1) about 2 to about 4 or (2) about 10 to about 12.

7. The composition of claim 6 wherein (i) when said pH is about 2 to about 4, said pH is adjusted by an acidic component present in an amount of about or greater than 12 wt. % based on actives of said acidic component and (ii) when said pH is about 10 to about 12, said pH is adjusted by an alkaline component present in an amount of about or greater than 1 wt. % based on actives of said alkaline component.

8. The composition of claim 1 wherein said at least one component which is corrosive by nature is one or more of a surfactant, disinfectant, antibacterial, and insecticide.

9. The composition of claim 1 wherein said blend comprises (i) two surfactants or (ii) a surfactant and a salt.

10. The composition of claim 1 wherein said at least one surfactant is nonionic, anionic, cationic, amphoteric or zwitterionic, or mixtures thereof.

11. The composition of claim 1 wherein said surfactant is one or more of ethoxylated alcohols, alkyl phenol ethoxylates, alkyl phenol propoxylates, sorbitol propoxylates, alcohol ethylene oxide- and propylene oxide-containing surfactants, alkyl polyglucosides, fatty alcohol polyglycol ethers, glycerol ethoxylates, linear alkyl sulfates and acid forms thereof, alcohol ether sulfates and acid forms thereof, alkyl benzene sulfonates and acid forms thereof, alcohol sulfates and acid forms thereof, alkyl- and alkylaryl-alkoxylated carboxylic acids and acid forms thereof, quaternary amines, betaines, sultaines, and glycines.

12. The composition of claim 1 wherein said thickening component is one of the following components: natural gums; rheology modifying polymers; shear thinning polymers; cellulose thickeners; clays; silicate compounds; associative thickeners; sodium laureth sulfate blended with a salt; an ethoxylated undecyl alcohol blended with a fatty alcohol polyglycol ether based on a C16-C18 alcohol; a C11 oxo-alcohol polyglycol ether with 7 EO blended with a C16-C18 fatty alcohol polyglycol with 25 EO; ethoxylated amides; and polyethylene glycols.

13. The composition of claim 1 wherein said surfactant is present in an amount of from about 3 to about 70 wt. %.

14. A concentrate composition having reduced corrosivity including one or more ingredients corrosive in nature, comprising
(a) about 10 to about 50 wt. % of a surfactant;
(b) at least one component which is corrosive by nature and present in an amount which renders said composition corrosive in absence of (c), wherein if one or more of said at least one surfactant is corrosive by nature at a level to make the composition corrosive, said at least one component which is corrosive by nature is optional;
(c) a thickening component comprising (1) at least one thickening agent or (2) a blend of two or more components which self-thicken when present as a blend, wherein said thickening component is present to provide a viscosity to said composition so that said composition is non-corrosive;
(d) one or more of water and at least one solvent; and
(e) optionally, a fragrance component;
wherein said composition has a pH of about 2 to about 4 or of about 10 to about 12;
wherein said composition has a viscosity of about 1000 to about 12,000 centerpoise (cps);
wherein said composition which is initially corrosive is modified to have a level of ocular irritation reduced as compared to said composition not containing said thickening component: and
wherein in absence of said thickening component, said level of ocular irritation of said composition falls into a category under a bovine cornea opacity and permeability (BCOP) method which characterizes said composition as corrosive.

15. The concentrate composition of claim 14 wherein said composition is a cleaning composition.

16. The concentrate composition of claim 14 wherein (i) when said pH is about 2 to about 4, said pH is adjusted by an acidic component present in an amount of about or greater than 12 wt. % based on actives of said acidic component and (ii) when said pH is about 10 to about 12, said pH is adjusted by an alkaline component present in an amount of about or greater than 1 wt. % based on actives of said alkaline component.

17. The concentrate composition of claim 14 wherein said at least one component which is corrosive by nature is one or more of a surfactant, disinfectant, antibacterial, and insecticide.

18. The concentrate composition of claim 14 wherein said blend comprises (i) two surfactants or (ii) a surfactant and a salt.

19. The concentrate composition of claim 14 wherein said at least one surfactant is nonionic, anionic, cationic, amphoteric or zwitterionic, or mixtures thereof.

20. The concentrate composition of claim 14 wherein said surfactant is one or more of ethoxylated alcohols, alkyl phenol ethoxylates, alkyl phenol propoxylates, sorbitol propoxylates, alcohol ethylene oxide- and propylene oxide-containing surfactants, alkyl polyglucosides, fatty alcohol polyglycol ethers, glycerol ethoxylates, linear alkyl sulfates and acid forms thereof, alcohol ether sulfates and acid forms thereof, alkyl benzene sulfonates and acid forms thereof, alcohol sulfates and acid forms thereof, alkyl- and alkylaryl-alkoxylated carboxylic acids and acid forms thereof, quaternary amines, betaines, sultaines, and glycines.

21. The concentrate composition of claim 14 wherein said thickening component is one of the following components: natural gums; rheology modifying polymers; shear thinning polymers; cellulose thickeners; silicate compounds; associative thickeners; clays; sodium laureth sulfate blended with a salt; an ethoxylated undecyl alcohol blended with a fatty alcohol polyglycol ether based on a C16-C18 alcohol; a C11 oxo-alcohol polyglycol ether with 7 EO blended with a C16-C18 fatty alcohol polyglycol with 25 EO; ethoxylated amides; and polyethylene glycols.

22. The concentrate composition of claim 14 wherein said viscosity is from about 1000 to about 8000 cps.

23. The concentrate composition of claim 14 wherein said at least one solvent is present in an amount of from about 2 to about 8 wt. %.

24. The concentrate composition of claim 14 wherein said fragrance component is present in an amount of about 5 to about 8 wt. %.

25. A method of reducing corrosivity in a composition containing one or more ingredients which are corrosive by nature without removing said ingredients and without reducing amounts of said ingredients, comprising—
  (a) combining to provide said composition (1) at least one surfactant, and (2) at least one component which is corrosive by nature and present in an amount which renders said composition corrosive in absence of (b), wherein if one or more of said at least one surfactant is corrosive by nature and present at a level to make the composition corrosive, said at least one component which is corrosive by nature of (2) is optional, and
  (b) adding a thickening component comprising (i) a thickening agent or (ii) a blend of two or more components which self-thicken when present as a blend, wherein said composition has a pH of about 2 to about 12; and wherein said composition is provided with a viscosity in a range of about 100 to about 1,250,000 centipoise (cps) as sufficient to render said composition non-corrosive; and
  wherein said composition in absence of said thickening component has a level of ocular irritation so as to fall into a category under a bovine cornea opacity and permeability (BCOP) method which characterizes said composition as corrosive.

26. The method of claim 25 wherein said composition is a cleaning composition.

27. The method of claim 26 wherein said cleaning composition is present in concentrate form and is diluted in use, and wherein said pH of said concentrate form is either about 2 to about 4 or about 10 to about 12.

28. The method of claim 27 wherein (i) when said pH is about 2 to about 4, said pH is adjusted by an acidic component present in an amount of about or greater than 12 wt. % based on actives of said acidic component and (ii) when said pH is about 10 to about 12, said pH is adjusted by an alkaline component present in an amount of about or greater than 1 wt. % based on actives of said alkaline component.

29. The method of claim 25 wherein said at least one component which is corrosive by nature is one or more of a surfactant, disinfectant, antibacterial, and insecticide.

30. The method of claim 25 wherein said blend comprises (1) two surfactants or (ii) a surfactant and a salt.

\* \* \* \* \*